United States Patent
Puppels et al.

(10) Patent No.: US 7,656,522 B2
(45) Date of Patent: Feb. 2, 2010

(54) DEPTH SELECTIVE PH MEASUREMENT AND UV EXPOSURE MEASUREMENT

(75) Inventors: Gerwin Jan Puppels, Rotterdam (NL); Peter Jacobus Caspers, Rotterdam (NL); Gerhardus Wilhelmus Lucassen, Eindhoven (NL)

(73) Assignee: River Diagnostics B.V., Rotterdam (NL)

( * ) Notice: Subject to any disclaimer, the term of this patent is extended or adjusted under 35 U.S.C. 154(b) by 868 days.

(21) Appl. No.: 10/506,056

(22) PCT Filed: Feb. 28, 2002

(86) PCT No.: PCT/NL02/00132

§ 371 (c)(1),
(2), (4) Date: Jan. 24, 2005

(87) PCT Pub. No.: WO03/073082

PCT Pub. Date: Sep. 4, 2003

(65) Prior Publication Data

US 2005/0117150 A1 Jun. 2, 2005

(51) Int. Cl.
*G01J 3/44* (2006.01)
(52) U.S. Cl. .................................................... 356/301
(58) Field of Classification Search ................. 356/301; 600/309, 310, 361
See application file for complete search history.

(56) References Cited

U.S. PATENT DOCUMENTS 6,542,762 B1 * 4/2003 Alam et al. ................. 600/310
7,113,814 B2 * 9/2006 Ward et al. ................. 600/310

FOREIGN PATENT DOCUMENTS

WO    WO 00 78217    12/2000

OTHER PUBLICATIONS

Caspers P J et al: "In Vivo Confocal Raman Microspectroscopy of the Skin: Noninvasive Determination of Molecular Concentration Profiles", Journal of Investigative Dermatology, vol. 116, No. 3, Mar. 2001, pp. 434-442, XP002220321 cited in the application p. 436, right-hand column, paragraph 4.

* cited by examiner

*Primary Examiner*—L. G Lauchman
(74) *Attorney, Agent, or Firm*—Hoffman & Baron, LLP

(57) ABSTRACT

A Raman spectrum is measured inside animal tissue, such us human skin tissue, at a selected depth from a surface the tissue. A pH value is computed using a function that assigns a pH value as a function of the measured Raman spectrum. The computation may involve computing a number representing a ratio of concentrations of a protonated and a deprotonated version of a chemical substance from the Raman spectrum and generating pH information on the basis of said number. The chemical substance is for example a form of Urocanic acid (UCA). UV exposure is measured from the weight of the spectrum of cis-UCA.

20 Claims, 7 Drawing Sheets

DEPTH SELECTIVE PH MEASUREMENT AND UV EXPOSURE MEASUREMENT

This application is the U.S. National Phase of International Application Number PCT/NL02/00132 filed on 28 Feb. 2002, which is incorporated herein by reference.

FIELD OF THE INVENTION

The invention relates a method and apparatus for depth selective pH measurement in animal tissue (animal tissue being understood to include human tissue). The invention also relates to a method and apparatus for measuring effects of exposing skin tissue to UV irradiation.

BACKGROUND ART pH, or more generally the concentration of free Hydrogen atoms, is an important parameter of tissue such as skin. pH at the skin surface differs from individual to individual and is moreover dependent on external influences such as the application of cleansing products or other personal care products, such as deodorants. Cleansing products (water, soaps, shampoos etc) can have a pronounced effect on skin pH which only slowly returns to the pH-value before cleaning. In addition there is a large difference between pH of the surface of skin and the pH of deeper layers of the skin, because a large difference in pH exists between the skin surface and the vital epidermis. This pH difference is maintained by the stratum corneum which is the outermost skin layer. For the development of such products it would be desirable to monitor their effects on the pH of the skin.

Known methods of measuring pH involve for example the application of chemical pH indicators or electrical measurements, wherein the potential difference between an electrode on the skin and a reference electrode is measured. An article by K. I. Mullen, D. Wang, L. G. Crane, and K. T. Carron, titled "Determination of pH: SERS Fiber Optic probes", published in Analytical Chemistry 64, page 930 (1992) describes a technique for measuring pH in water using a pH indicator molecule attached to the end of an optical fiber. Raman scattered light from the molecule is gathered through the fiber and analysed. With these presently available methods non-invasive skin pH measurements with the known methods are limited to the skin surface. Such measurements are unsatisfactory because of the large difference between pH of the surface of skin and the pH of deeper layers of the skin. Invasive techniques are needed to measure the pH below the surface of the skin with these known methods, or more generally to measure pH as a function of depth in the skin. The disadvantage of invasive techniques is that the pH may be affected by the invasive technique and/or that otherwise skin physiology is disturbed. Moreover it is difficult to monitor ongoing changes in pH.

Accordingly, there exists a need for a method of measuring pH at selected depths in skin tissue without using invasive techniques, so that the normal chemical processes in the skin are not influenced by the measurements.

An article titled "In Vivo Confocal Raman microspectroscopy of the Skin: Non-invasive Determination of Molecular Concentration Profiles" published in March 2001 in the Journal of Investigative Dermatology 116 pages 434-442 (2001), and authored by Peter J. Caspers, Gerald W. Lucassen, Elizabeth Carter, Hajo Bruining and Gerwin J. Puppels describes depth selective Raman spectroscopy of skin tissue. This article is incorporated herein by way of reference.

Raman spectroscopy is a non-invasive technique that involves illuminating material with essentially monochromatic light of a first wavelength and observing the intensity of light that has been inelastically scattered by the material, as a function of wavelength of the inelastically scattered light. The spectrum of the inelastically scattered light is a composite of contributions of the different chemical species in the material.

In principle, each chemical species provides its own characteristic contribution to the spectrum, in proportion to its concentration. This makes it possible to determine at least the relative concentrations of chemical species in the material. Raman Spectroscopy can be made depth and/or location sensitive by focussing the monochromatic light at a certain depth or location and/or gathering inelastically scattered light selectively from a depth or location.

Unfortunately, free protons do not have a measurable Raman spectrum. Therefore Raman spectroscopy cannot be used to measure light that is inelastically scattered by protons. However, the article mentions a discovery by the inventors of the present invention that among a great many other contributions the Raman spectrum of light scattered by skin tissue naturally contains a detectable contribution of UCA (Urocanic acid). The concentration of UCA in the stratum corneum depends on many variable factors. In addition the protonation of UCA varies significantly in the pH range that may be encountered in the skin (pH's typically range from 4.5 to 7). The Raman scattering spectrum of UCA is pH dependent.

SUMMARY OF THE INVENTION

Amongst others it is an object of the invention to provide for a method and apparatus for depth selective measurement of pH in animal tissue and in particular in human skin tissue which leaves the tissue intact.

Amongst others it is an object of the invention to provide for a method and apparatus for depth selective measurement of pH in animal skin tissue.

Amongst others it is a further object of the invention to provide for a method and apparatus for depth selectively measuring pH in animal tissue as a function of position transverse to the depth in the tissue.

Amongst others it is an object of the invention to make use of the published discovery that the Raman spectrum of light scattered by skin tissue contains a contribution of UCA that is strongly pH dependent.

Amongst others it is another object of the invention to provide for a technique for measuring an indication of a dose of UV irradiation received by skin tissue.

Amongst others it is another object of the invention to provide for a technique for measuring an indication of potential health damage by UV irradiation received by skin tissue.

Amongst others it is another object of the invention to provide for a technique to determine the efficacy of sun protection devices or sun screens.

According to one aspect of the invention a Raman spectrum is obtained from in a depth dependent way from inside the skin, for example at a selected depth by focussing a lightsource at the selected depth, or from a selected range of depths. From the measured spectrum a pH value is computed using a function that assigns a pH value as a function of the measured Raman spectrum.

pH information is computed on the basis of said number. The function may compute for example a ratio of the weights with which pH dependent spectra of a chemical constituent of the skin at different pH values contribute to the measured spectrum and a pH value derived from this ratio is output. Although Raman spectroscopy requires cumbersome calibration to determine absolute concentrations from the weights, the determination of ratio's does not require that calibration. The computed pH value may be output for display to a human operator, in the form of a number or as a graph of pH versus depth, so as to enable the operator to evaluate skin conditions for example after application of therapeutic or cosmetic substances to the skin or to diagnose skin diseases. The computed pH value may also be used for example for automatic dosage of application of substances to the skin, to switch supply of one or more of the substances on or off dependent on the measured pH at a certain depth in the skin, or to control the concentration with which the substances are supplied dependent on the measured pH.

Preferably, the concentrations of the protonated and deprotonated version of a form of urocanic acid (UCA), more preferably trans-urocanic acid, are used to compute the pH value from the spectrum but in other embodiments cis-urocanic acid or histidine or any other tissue constituent that has a pH dependent spectrum in the range of pH values that occur in the tissue may be used, or a constituent comprising a mixture of such substances may be used.

In a preferred embodiment a ratio of concentrations of protonated and deprotonated versions is computed by fitting a set of weights with which a number of predetermined spectra of contribute to the measured spectrum, the predetermined spectra at least including two spectra of a constituent that has a pH dependent spectrum, the two spectra corresponding to different pH values. Preferably, the predetermined spectra also include Raman spectra of major chemical components that have been found to occur in the type of tissue under study.

However, it is not necessary to use explicit spectra nor is it necessary to use explicit fitting. It has been discovered that pH can be computed using a function of the set of measured intensities that represent the Raman spectrum of animal tissue. Fitting is merely one way of defining this function. As an alternative this function may be computed without fitting. For this purpose one may use an approximate function of the intensity values, whose input/output relation may be tuned by adjusting a number of adjustable parameters. The parameters are set in advance so that the result of the function approximates the pH value given a measured spectrum. Such a function will generally compute the pH from the entire spectrum, not just from the contribution of a single chemical, like UCA.

Similar techniques may be used to measure health damaging effects of UV irradiation. According to another aspect of the invention a method of measuring a health damaging effect of UV irradiation in skin tissue, is provided that comprises measuring a Raman spectrum of a part the tissue selected dependent on a depth from a surface of the tissue;

computing an effect of UV irradiation using a function of UV irradiation dependent aspects of the measured Raman spectrum.

It has been found that the Raman spectrum of skin tissue depends in a measurable way on the relative concentrations of cis-UCA and trans-UCA. Cis-UCA is formed from trans-UCA under the influence of UV irradiation. The concentration of cis-UCA is suspected to be arm agent in health damaging effects of UV irradiation. At least it is strongly correlated with these health damaging effects. Hence Raman spectroscopy provides for a method and apparatus that can help people to avoid health damage due to UV irradiation by providing a monitor for the rise of such damage. All embodiments of the method and apparatus for measuring pH apply mutatis mutandis to measurement of health damaging effects of UV irradiation as well. Also similar computer programs may be used mutatis mutandis for computing the health damaging effect.

BRIEF DESCRIPTION OF THE DRAWINGS

These and other objects and advantageous aspects of the method and apparatus according to the invention will be described in more detail in a non-limitative way using the following drawing

DETAILED DESCRIPTION OF THE INVENTION

Figure 1:
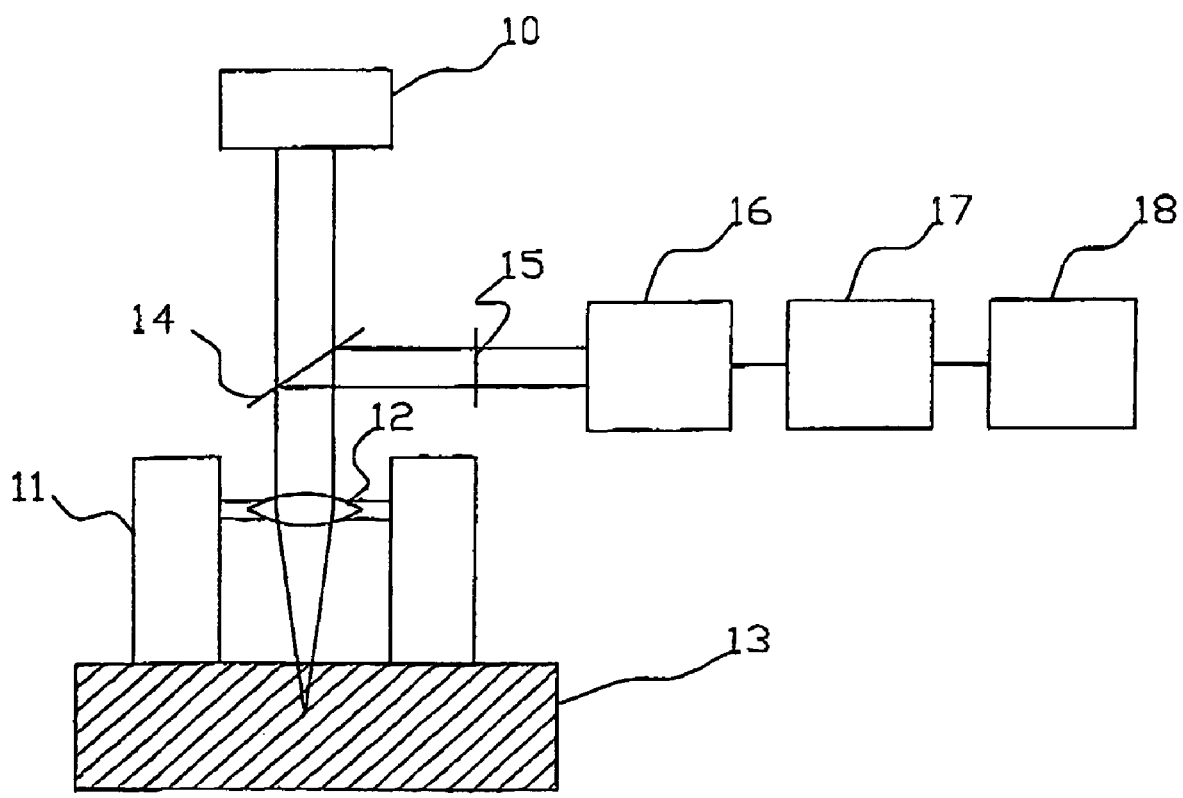
FIG. 1 shows a depth selective pH measuring apparatus

FIG. 1 schematically shows an apparatus for selectively measuring pH in skin tissue 13. The apparatus comprises a light source 10, a height adjustment unit 11, a focussing lens 12, a splitter 14, an output filter 15, a spectrometer 16, a computing device 17 and an output device 18. The light source 10 is arranged to illuminate the skin tissue 13 via splitter 14 and lens 12. Height adjustment wait 11 is arranged to adjust the position of lens 12 relative to skin tissue 18. Spectrometer 16 is arranged to receive scattered light from skin tissue 13 via lens 12, splitter 14 and output filter 15. Spectrometer 16 has an output coupled to computing device 17, which in turn has an output coupled to output device 18.

The arrangement of a light source, focussing lens, splitter 14, output filter 15 and spectrometer forms a conventional Raman spectrometer arrangement. Any variation of such an arrangement may be used. For example various additional elements such as mirrors and filters may be added to in the light path in light source 10, spectrometer 16 or between these devices. For example the light path may contain imaging optics (not shown) to form an image of the skin at the depth at which the laser light is focused in an image plane. An aperture (not shown) may be provided in the image plane, such that the location where light from light source 10 is focused in the skin 18 is imaged onto the aperture. The size and/or shape of the aperture may be selected to limit the measurement volume to a well defined location in the skin. Light passed by the aperture is fed to spectrometer 16. Preferably a multi-channel detector is used in spectrometer 16, to measure the intensity of scattered light for a plurality of wavelength channels in parallel.

If desired one or more optical fibers may be used in part or all of the light path from source 10 to skin 13 and from there back to spectrometer 16, to conduct the incoming light and/or the scattered light.

Computing device 17 may be any suitably programmed computer. The program with instructions to cause the computer to process the Raman measurement may be a firmware program present in non-volatile memory in the computing device 17, or a program loaded from a program carrier such as a CD-ROM, a floppy disk etc.

In operation, essentially monochromatic light from light source 10 is focussed onto skin tissue 13 by lens 12. The light source is preferably a monomode laser with an emission wavelength between 680 nm and 860 nm. Height adjustment unit 11 is adjusted so as to focus the light at a selected depth. Light scattered by skin tissue 13 from a location where the light is in focus is fed to spectrometer 16. Elastically scattered light, that is, light with the same wavelength as the main wavelength of light source 10 is filtered out by output filter 15. Spectrometer 16 analyses the spectrum of the inelastically scattered scattered light, producing a collection of light intensity measurements, each for a respective wavelength. Computing device 17 reads the results of the light intensity measurements from spectrometer 16.

Figure 2:
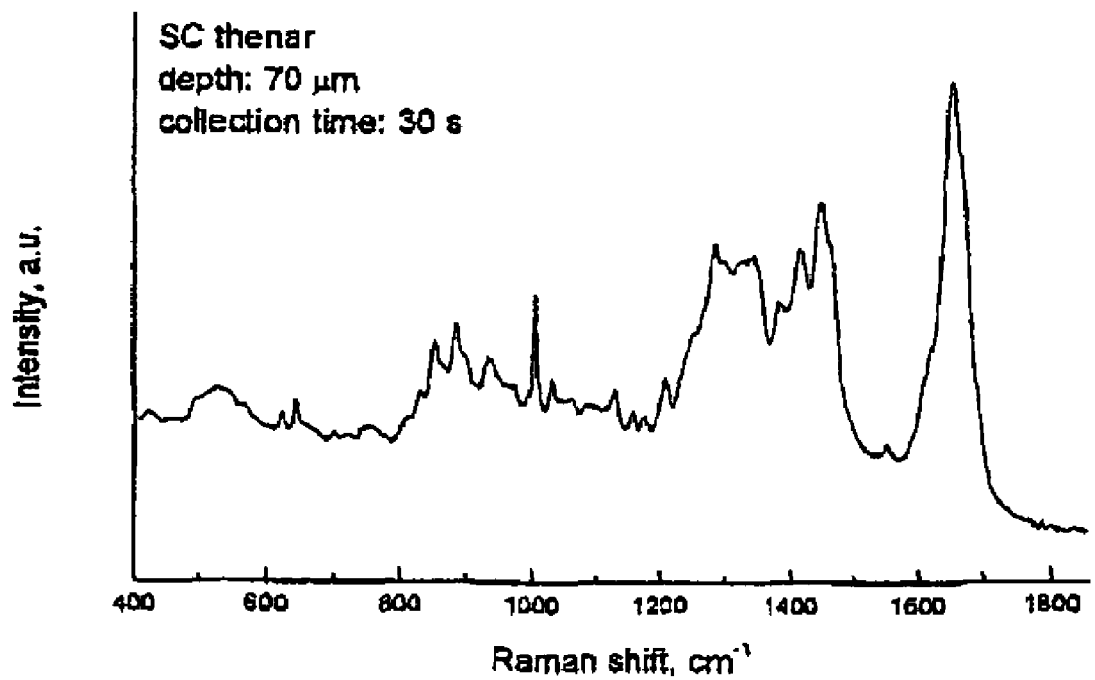
FIG. 2 shows a Raman spectrum of human skin tissue

FIG. 2 shows a typical example of a measured spectrum of inelastically scattered light as a function of wavelength (expressed in terms of wavenumber shift, which defined as $(1/\lambda\text{source}-1/\lambda)*10^7)$ where $\lambda$ [in m] is the wavelength of the inelastically scattered light) measured with light focused at a depth 70 micrometer below the surface of the skin 13. It will be observed that the spectrum contains a considerable amount of structure. This structure is characteristic of the mixture of chemical substances present in the region where light is inelastically scattered.

It has been discovered that in skin tissue one of these substances that contribute to the structure of the spectrum is Urocanic acid (UCA). UCA is formed in the skin from Histidine under influence of the enzyme Histidase and diffuses from the vital epidermis into the stratum corneum. Therefore the concentration of UCA in the stratum corneum depends on many variable factors. UCA is also present in the liver and may be used to measure pH inside liver tissue.

Figure 3:
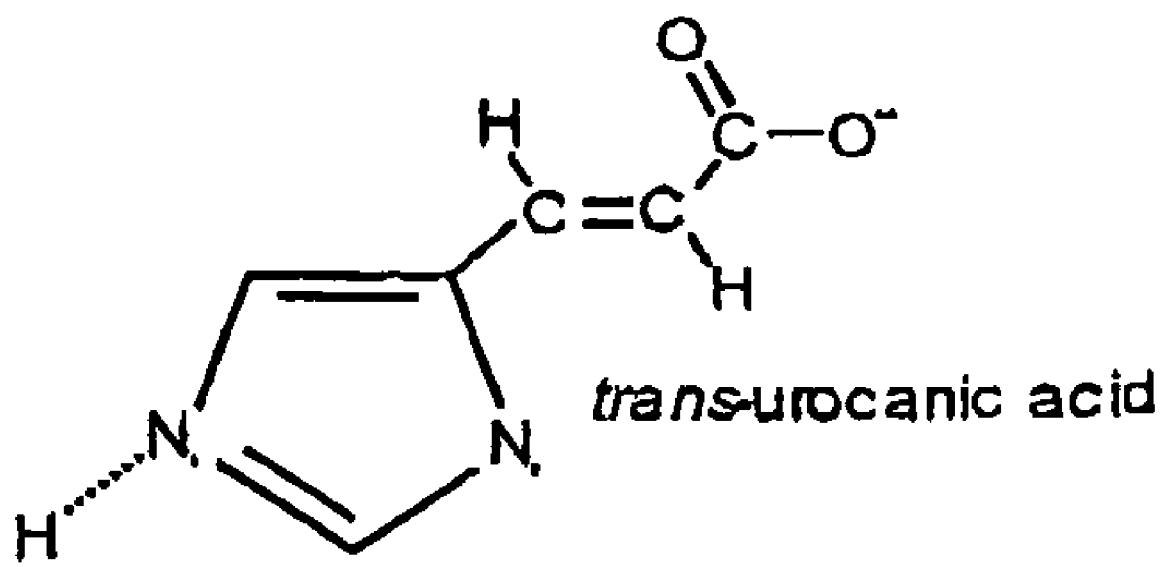
FIG. 3 shows a structural formula of trans-UCA

FIG. 3 shows a structural formula of the protonated form of trans-Urocanic Acid (UCA). The acidic properties of UCA are mainly due to a proton (H) bound to an imidazole ring. In the pH range of interest in the skin (4 to 7.5) trans-UCA has a pK value of 6.1 for protonation of the imidazole ring. At the lowest pH values that may occur in skin tissue most of UCA remainder molecules have a proton bound to their imidazole ring. At the highest pH values that occur in skin tissue the imidazole rings of most UCA remainder molecules are deprotonated.

Figure 4:
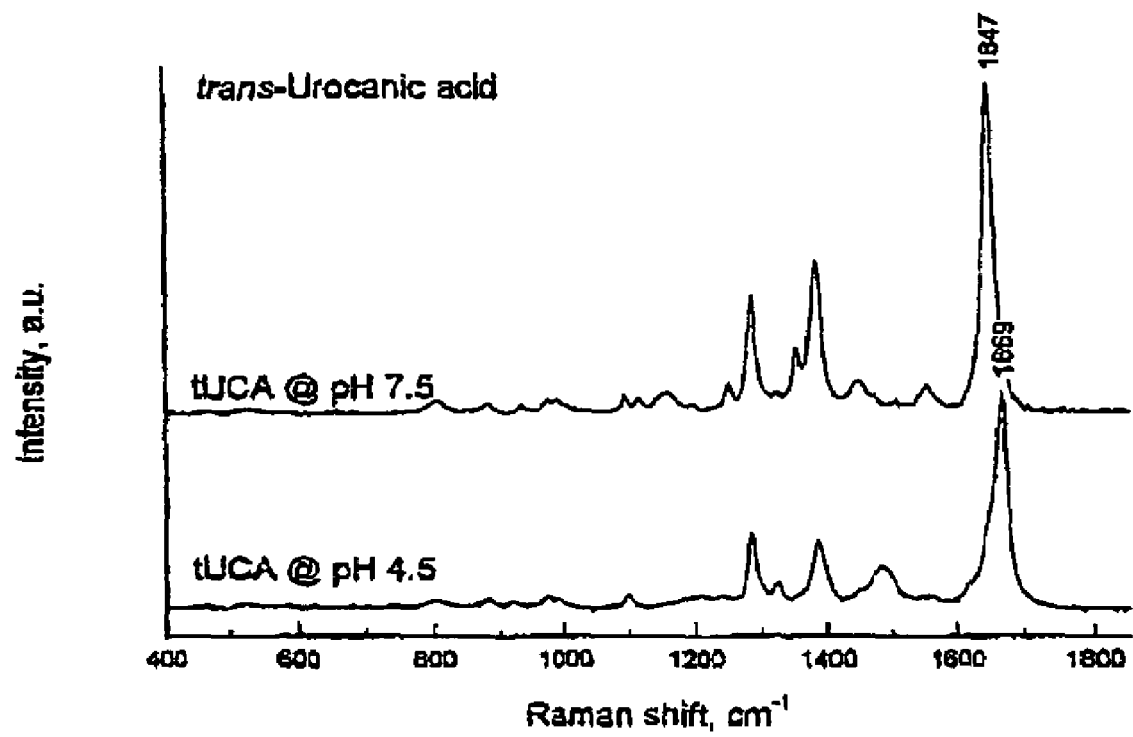
FIG. 4 shows Raman spectra of UCA

FIG. 4 shows Raman inelastic scattering spectra of isolated trans-UCA measured at pH values of 4.5 and 7.5. It can be seen that the spectra differ. Comparing FIG. 4 with FIG. 2 will show that trans-UCA is not the sole contributor to the Raman spectrum of skin tissue (it must be noted that the peak between 1600 and 1700 cm−1 in FIG. 2 is only partly due to contributions of UCA; it does not change as pronouncedly with pH as the peak in the spectrum of UCA). Also the pH dependence of the Raman spectrum due to the pH dependence of UCA is quite small. Nevertheless it has been realized that the spectrum of UCA can be used to measure pH in skin tissue.

Computing device 17 is programmed to compute the pH value of the skin tissue at the depth where the light is inelastically scattered from the measured Raman spectrum of the inelastically scattered light.

Figure 5:
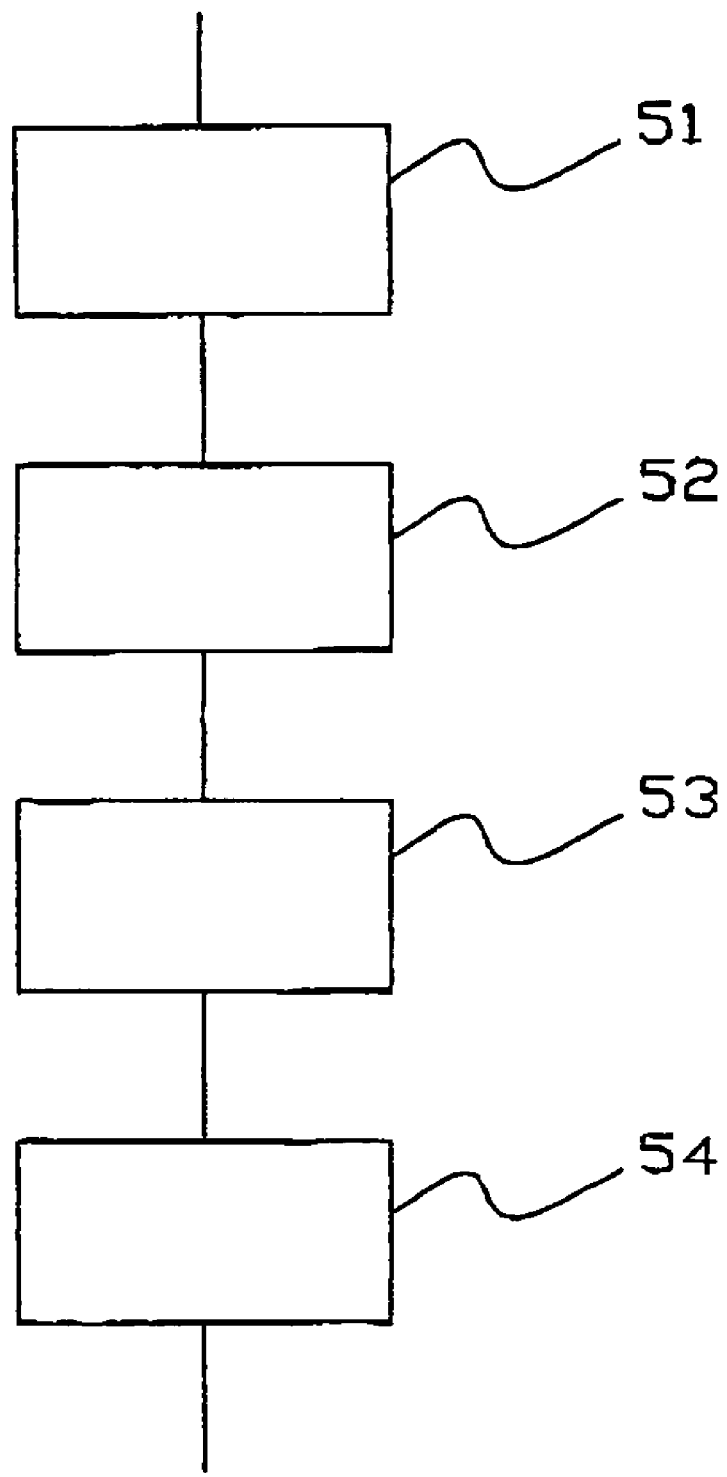
FIG. 5 shows a flow-chart of a method of measuring pH FIG. 6a,b show resulting measurements as a function of depth

FIG. 5 shows a flow-chart of a method of measuring pH in skin tissue. In a first step 51, computing device reads information about the spectrum from spectrometer 16. Computing device 17 pre-processes the information to correct for known wavelength dependency of the sensitivity of the instrument (involving for example throughput through the light path and the efficiency of spectrometer 16), and associates measured spectral intensity values with respective wavelengths.

In a second step 52, computing device 17 determines the weights with which different Raman scattering spectra of different chemical species that are expected to be present in the skin tissue contribute to the measured spectrum. For this purpose, computing device 17 stores data describing spectra of a number of such chemical species, including the spectrum of trans UCA at different pH values, for example pH values of 4.5 and 7.5. Known spectra may be used to provide the stored spectra for this purpose or the stored spectra may be provided by measuring spectra of UCA at different pH during a calibration stage. Instead of spectra measured at different pH values, computed spectra may be used that form extrapolations of spectra measured at different pH values. Other chemical species for which computing device 17 stores spectra, because they have been found to occur at one time or another in relevant quantities in the skin include pyrrolidone carboxylic acid, arginine, ornithine, citrulline, serine, proline, glycine, histidine, alaninine, lactate, urea, water, keratine, ceramides and cholesterol. Preferably spectra of all these compounds, or combinations thereof (when the compounds occur in predetermined ratio's) may be used during fitting.

The computing device 17 preferably assigns weights to each of the stored spectra by means of a least square fit, selecting a set of weights that minimizes a squared measure of difference between the measured spectrum and a weighted sum of the stored spectra. Thus, in the second step 52 the computing device 17 generates, amongst others, weights associated with spectra of UCA taken at different pH values.

In third step 53 computing device 17 computes a ratio of the concentrations of the protonated and deprotonated form of UCA from the weights computed in second step 52. For example, when stored spectra of for the same concentration of UCA at pH values of 4.5 and 7.5 are used to fit the measured spectrum (at which values UCA is nearly completely protonated and deprotonated respectively), the ratio R may be computed from $$R=(w1*C1)/(w2*C2)$$

where w1 and w2 are the weights computed for the two stored spectra of UCA and C1 and C2 are the concentrations of UCA in the samples from which the stored spectra where obtained. Of course, instead of spectra obtained at pH values where UCA is nearly completely protonated and deprotonated respectively, spectra at other pH values may be used. If a first spectrum is assigned a weight wa and corresponds to concentrations Ca1 and Ca2 of the protonated and deprotonated version respectively, and a second spectrum is assigned a weight wb and corresponds to concentrations Cb1 and Cb2 of the protonated and deprotonated version respectively, then the ratio R may be computed from $$R=(wa*Ca1+wb*Cb1)/(wa*Ca2+wb*Cb2)$$

Similarly, if the reference spectra that are weighed to fit the measured spectrum correspond to mutually different but known concentrations, the weights are corrected proportionally to the known concentrations of the reference spectra. In fourth step 54 computing device 17 computes the pH value from the ration R and the known pK value (6.1) of UCA:

$$pH=pK+\log(R).$$

Computing device 17 outputs the measured pH value to output device 18 for further use. Output device 18 may output the pH value on a display screen that displays the measured pH value, but any other use may be made of the measured pH value. For example, the measured pH value might be used to control dosage of material applied to the skin surface.

Although the invention has been described by way of example using the algorithm of FIG. 5, it will be appreciated that many variations are possible that all allow computation of pH from the measured spectrum. For example, one might directly fit R or even the pH, instead of using the weights w as intermediates. In another example, instead of fitting the entire spectrum only part of the spectrum may be fitted or different parts of the spectrum may be weighted differently for example according to the extent to which they depend on pH.

Although the invention has been explained in terms of measurements using the pH dependence of the Raman spectrum of trans-UCA, other substances may be used. Trans UCA is preferred because it has been found to be available in sufficient concentration in skin tissue. However, without deviating from the invention pH dependent spectra of other materials may be used, such as for example the protonated and deprotonated form of histidine, or of cis-UCA. These materials have also been found suitable for measuring pH in skin tissue under some circumstances. One may even use a combination of these substances to determine pH.

The method described in FIG. 5 defines a function that assigns a pH value as a function of the intensity values of the measured spectrum. Of course, the procedure of fitting weight values in a weighted sum of a number of predetermined spectra to minimize the difference with the measured spectrum, followed by computing pH from the weight values of two specific spectra is merely one way of computing this function. In yet another example this function is computed without explicit fit. For this purpose an approximate function may be used with a number of adjustable parameters. The parameters are set in advance so that the function approximates the ratio R given a measured spectrum.

Many ways of defining such an approximate function exist. For example, one may use a function defined by the operation of a computerized neural network. In this case a conventional neural network "training" procedure may be used to select the parameters of the function so that the network computes the pH value. In this case, a number of spectra taken at different pH values is used in the training procedure, together with the corresponding pH values, which may be obtained for example using the minimization method described in the preceding, or by other types of measurement, or from information about the preparation of the specimen from which the spectra where taken.

But of course, instead of the functions that simulate a neural network, any other type of parameterised function with appropriately selected parameters may be used, such as for example a polynomial or a ratio of multinomials (a multinomial is a function whose dependence on each of the various intensity values from the measured spectrum is polynomial) etc. Whatever function is used to assign pH, it will be appreciated that thus the function will generally compute the pH from the entire spectrum, not just from the contribution of a single chemical, like UCA.

Preferably computing device 17 is coupled to height adjustment unit 11 to control the depth of the skin at which light from light source 10 is focussed. In this case, a scan of pH versus depth may be made, by repeatedly adjusting the position of lens 12 relative to skin 13, measuring an inelastic scattering spectrum and computing pH according to the steps of FIG. 5.

Figure 6A:
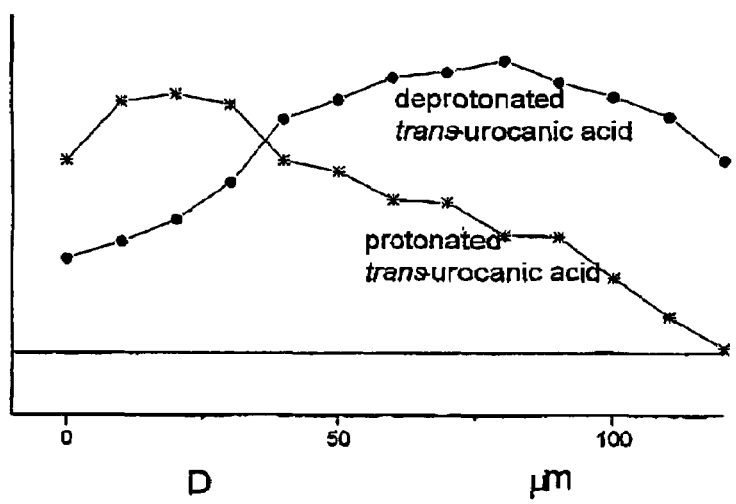
Figure 6B:
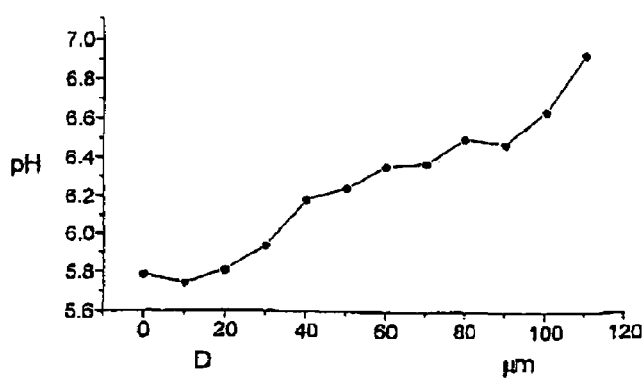

FIG. 6a shows examples of weight values (in arbitrary units) computed for the two UCA spectra as a function of depth D (distance to skin surface) and FIG. 6b shows the corresponding pH values.

Preferably, the apparatus of FIG. 1 is also provided with a mechanism for scanning the measurement position transverse to the direction perpendicular to the skin. This may be realized using scannable mirrors. Such a transverse position and depth dependent measurement may be combined with other type of transverse position dependent measurement, such as for example simple optical imaging, so as to make it possible to correlate pH variations with other observable phenomena.

Figure 7:
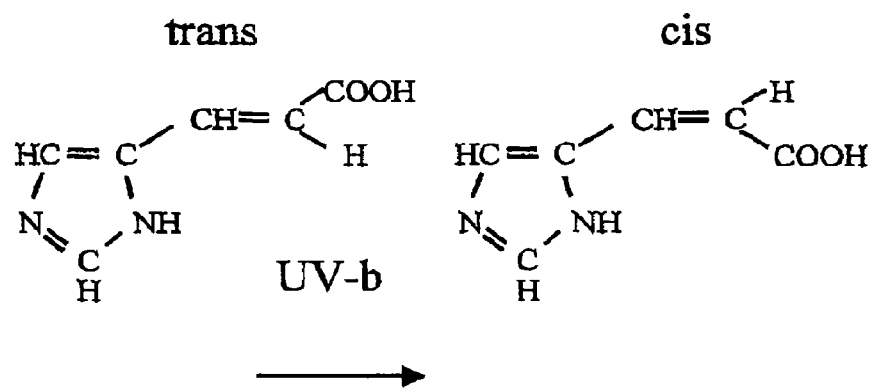
FIG. 7 shows structural formulas of cis-UCA and trans UCA

FIG. 7 shows structural formulas of cis-UCA and trans-UCA (cis-UCA is an isomer of trans-UCA). Trans-UCA is affected by UV (Ultra Violet) irradiation: under the influence of UV light trans-UCA is converted into cis-UCA. Conversion of trans-UCA into cis-UCA in the stratum corneum of the skin is thought to be an important agent in the health damaging effect of UVB irradiation inside the skin. A higher ratio (relatively more cis-UCA) occurs upon exposure to UVB irradiation. After irradiation the ratio drops only slowly: it is assumed that the health damaging effects persist until the ratio has dropped sufficiently. In any case, increases in the ratio of the cis-UCA concentration and the trans-UCA concentration inside the skin is strongly correlated with health damaging effects of UV light.

It has been found that cis-UCA formation can be determined from the Raman spectrum of the skin.

Figure 8:
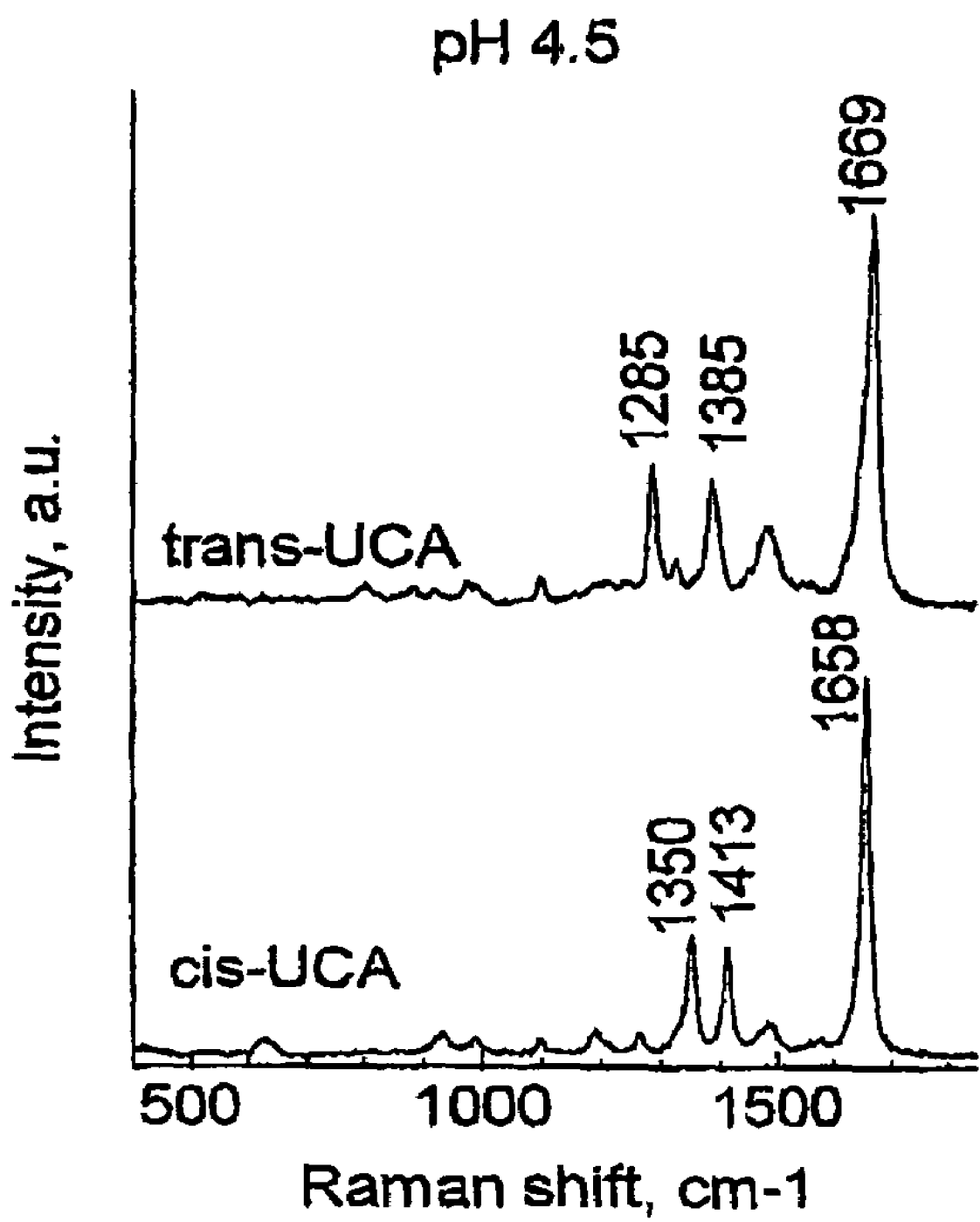
FIG. 8 shows Raman spectra of cis-UCA and trans-UCA

FIG. 8 shows Raman spectra of trans-UCA and cis-UCA. The overall Raman spectrum of skin tissue depends detectably on the ratio of the concentration of cis-UCA to the concentration of other substances in the skin. Therefore, measurement of this ratio using depth selective Raman spectroscopy can advantageously be used to monitor health damaging effects of UV irradiation in a non-invasive way.

An apparatus and process for performing this measurement works basically in the same way as the apparatus and process for pH measurement, but instead of the weights assigned to the spectra of the protonated and deprotonated version of trans-UCA the weights assigned to the spectra of cis-UCA and a reference substance (preferably trans-UCA) are used to determine information about the concentration of cis-UCA. Of course, instead of fitting an adapted function may be used for this purpose as described for the pH measurement.

The information about the concentration of cis-UCA is used to asses the extent to which UV irradiation has affected the skin tissue.

Any reference substance may be used but preferably the combination of the spectra of the protonated versions of cis-UCA and trans-UCA or the deprotonated versions of cis-UCA and trans-UCA are used for this. This allows for the elimination of pH dependent errors since the logarithms of the ratio of the concentrations of overall cis-UCA and trans-UCA differs from the logarithm of the concentrations of (de-)protonated cis-UCA and trans-UCA by the predetermined difference of the pK values of cis-UCA and trans-UCA (pKcis-pKtrans=0.9). Moreover, since cis-UCA is formed from trans-UCA under influence of UV light, the use of trans-UCA as a reference eliminates the effect of individual differences in trans UCA concentration on the measurement of the effect of UV irradiation.

If desired, the apparatus may select between using a measured ratio of the protonated concentrations or of the deprotonated concentrations, dependent on pH or rather on which version (protonated or deprotonated) yields larger weight values.

Such an apparatus or process that measures information about the concentration of a chemical substance that is generated under the influence of UV irradiation may be used to perform various further functions. For example, in a device for use by people who take sun-baths, the measured concentration ratio may be used to trigger and alarm signal such as an audible signal or a warning light when the ratio passes a predetermined threshold. The user is thereby enabled to terminate the sun-bath when there is more than a predetermined risk of health damage, or to apply a sun tan lotion with a strong blocking factor. Such an apparatus with an alarm may be part of an electric solarium, or it may be a stand alone device that may also be used outdoors, for example on the beach. More generally such an apparatus may be used by anyone that is exposed to UV irradiation, such as people that are outdoors for their work, to determine whether action should be taken against health hazards (e.g. by using sun blocking substances or ceasing to work outdoors until the ratio drops). The threshold for generating the alarm signal may be set to any value that has been determined to be indicative of potential health damage, either for the individual using the device or in general. The exact value of the threshold depends on the acceptable risk and may be set for example in future governmental health standards.

Similarly, the apparatus might have an output for outputting a graded signal derived from the measurement of the ratio of concentrations of trans-UCA and cis-UCA, for example in the form of a number of digits that represent a number indicative of the ratio, but other forms of signalling could be used, such as a meter with a pointing hand that is made to deviate according to the measured ratio, or even a display screen in which the color of an area is controlled dependent on the ratio, varying e.g. from green to red as the amount of cis-UCA increases. The output of the graded signal can be used for example to select a required blocking factor of sun-tan lotion, or to plan future exposure to sunlight.

Of course this process and apparatus for measuring an effect of UV irradiation can also be used in experiments to determine the effectivity of sun tan lotions, or more generally of substances that are used to protect the skin against the effects of UV irradiation. In this case one applies the substance to a skin area, irradiates the skin area with UV light and subsequently measures the ratio of the cis-UCA and trans-UCA concentration using Raman spectroscopy as described above. Preferably another area of the skin (preferably adjacent the first mentioned area) is treated similarly, except that the substance is not applied to the other area. The ratio's of cis-UCA and trans-UCA concentration measured for the two area's can then be compared to establish the differential effect of the substance. Of course a similar technique may be used in an apparatus for sun-bathers, by covering a part of the skin and measuring the concentration in the covered part and an uncovered part of the skin, to generate an alarm signal or a graded indication of UV effects.

We claim:

1. A depth selective method of measuring pH inside animal tissue, the method comprising measuring a Raman spectrum of a part of the tissue using a depth selective Raman spectrometer, said part being selected dependent on a depth from a surface of the tissue; computing a pH value using a function that assigns a pH value as a function of pH dependent aspects of the measured Raman spectrum.

2. A depth selective method of measuring pH in animal tissue according to claim 1, wherein said computing comprises computing a number representing a ratio of concentrations of a protonated and a deprotonated version of a chemical substance that are determined to contribute to the Raman spectrum and generating pH information on the basis of said number.

3. A method according to claim 2, wherein the chemical substance is a form of Urocanic acid.

4. A method according to claim 2, wherein the chemical substance is a form of Histidine.

5. A depth selective method of measuring pH inside animal tissue according to claim 2, wherein the number representing the concentrations of protonated and deprotonated versions of the chemical substance are computed by fitting weights so as to minimize a difference between the measured spectrum and a simulated spectrum that includes weighted contributions of a first spectrum and second spectrum of the chemical substance for different pH values.

6. A method according to claim 5, wherein the first and second spectra are spectra of a form of Urocanic acid.

7. A method according to claim 1, wherein the tissue is skin tissue.

8. An apparatus for depth selectively measuring pH inside animal tissue, the apparatus comprising a depth selective Raman spectrometer; a computing device arranged to compute a pH value using a function that assigns a pH value as a function of a pH dependent aspect of the measured Raman spectrum; an output for outputting a signal representing the computed pH value.

9. An apparatus according to claim 8, wherein said computing device is arranged to compute a number representing a ratio of concentrations of a protonated and a deprotonated version of a chemical substance from the Raman spectrum and generating pH information on the basis of said number.

10. An apparatus according to claim 9, wherein the chemical substance is a form of Urocanic acid.

11. An apparatus according to claim 9, wherein the number representing the concentrations of protonated and deprotonated versions of the chemical substance are computed by fitting weights so as to minimize a difference between the measured spectrum and a simulated spectrum with weighted contributions of a first spectrum and second spectrum of the chemical substance for different pH values.

12. An apparatus according to claim 11, wherein the first and second spectra are spectra of a form of Urocanic acid.

13. A computer program product comprising a computer readable medium having instructions for computing a pH value using a function that assigns a pH value as a function of a measured Raman spectrum and outputting pH information on the basis of said number.

14. A computer program product according to claim 13, wherein said computing comprises computing a number representing a ratio of concentrations of a protonated and a deprotonated version of a chemical substance from the Raman spectrum and generating pH information on the basis of said number.

15. A computer program product according to claim 14, wherein the number representing the concentrations of protonated and deprotonated versions of the chemical substance are computed by fitting weights so as to minimize a difference between the measured spectrum and a simulated spectrum with weighted contributions of a first spectrum and second spectrum of the chemical substance for different pH values.

16. A method of measuring an indication of a potentially health damaging effect of UV irradiation in skin tissue, the method comprising measuring a Raman spectrum of a part of the tissue selected dependent on a depth from a surface of the tissue using a depth selective Raman spectrometer; computing an effect of UV irradiation using a function of UV irradiation dependent aspects of the measured Raman spectrum.

17. A method according to claim 16, for measuring formation of cis-UCA in skin tissue as the indication of potentially health damaging effect wherein said computing comprises computing a number representing a ratio of concentrations of a form of cis-UCA and a reference substance that are determined to contribute to the Raman spectrum and generating irradiation information on the basis of said number.

18. A method according to claim 17, where the reference substance is a form of trans-UCA.

19. An apparatus for measuring effects of UV irradiation inside skin tissue, the apparatus comprising a depth selective Raman spectrometer; a computing device arranged to compute an effect of UV irradiation using a function UV dependent aspects of the measured Raman spectrum; an output for outputting a signal dependent on the computed effect.

20. An apparatus according to claim 18, wherein said computing device is arranged to compute a number representing a ratio of concentrations of a contributions of cis-UCA and trans-UCA to the Raman spectrum and generating the irradiation information on the basis of said number.

* * * * *

UNITED STATES PATENT AND TRADEMARK OFFICE
CERTIFICATE OF CORRECTION

PATENT NO. : 7,656,522 B2
APPLICATION NO. : 10/506056
DATED : February 2, 2010
INVENTOR(S) : Puppels et al.

It is certified that error appears in the above-identified patent and that said Letters Patent is hereby corrected as shown below:

ON THE COVER PAGE:

Now reads:     "Hoffman & Baron"

Should read:     --Hoffmann & Baron--

IN THE PATENT:

Column 3, line 57

Now reads:     "suspected to be arm agent"

Should read:     --suspected to be an agent--

Column 4, line 26

Now reads:     "Height adjustment wait 11"

Should read:     --Height adjustment unit 11--

Column 4, line 27

Now reads:     "relative to skin tissue 18"

Should read:     --relative to skin tissue 13--

Column 4, line 43

Now reads:     "The skin 18 is imaged"

Should read:     --The skin 13 is imaged--

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,656,522 B2  Page 1 of 1
APPLICATION NO. : 10/506056
DATED : February 2, 2010
INVENTOR(S) : Puppels et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1385 days.

Signed and Sealed this

Thirtieth Day of November, 2010

David J. Kappos
*Director of the United States Patent and Trademark Office*